US010189755B2

(12) United States Patent
Reeker et al.

(10) Patent No.: US 10,189,755 B2
(45) Date of Patent: Jan. 29, 2019

(54) OLIGOMERIZATION OF ETHENE IN SUPERCRITICAL MODE

(71) Applicant: Evonik Degussa GmbH, Essen (DE)

(72) Inventors: Helene Reeker, Dortmund (DE); Guido Stochniol, Haltern am See (DE); Dietrich Maschmeyer, Recklinghausen (DE); Stephan Peitz, Oer-Erkenschwick (DE); Jörg Schallenberg, Dorsten (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/605,170

(22) Filed: May 25, 2017

(65) Prior Publication Data
US 2017/0355651 A1 Dec. 14, 2017

(30) Foreign Application Priority Data

Jun. 10, 2016 (EP) ..................................... 16173939

(51) Int. Cl.
C07C 2/02 (2006.01)
C07C 2/24 (2006.01)
(Continued)

(52) U.S. Cl.
CPC .............. C07C 2/24 (2013.01); B01J 21/063 (2013.01); B01J 21/12 (2013.01); B01J 21/20 (2013.01);
(Continued)

(58) Field of Classification Search
CPC ..................................................... C07C 2/24
(Continued)

(56) References Cited

U.S. PATENT DOCUMENTS 2,581,228 A 1/1952 Bailey et al.
5,849,972 A 12/1998 Vicari et al.
(Continued)

FOREIGN PATENT DOCUMENTS

EP 1085001 A1 3/2001
EP 3045438 A1 7/2016
(Continued)

OTHER PUBLICATIONS

DE102009027408 (English translation) (Year: 2011).*
(Continued)

*Primary Examiner* — Philip Y Louie
*Assistant Examiner* — Aaron W Pierpont
(74) *Attorney, Agent, or Firm* — Nexsen Pruet PLLC; Philip P. McCann

(57) ABSTRACT

The disclosure describes the oligomerization of supercritical ethene. An essential aspect of the invention is that of mixing ethene with an inert medium and setting the conditions in the reaction such that both ethene and the inert medium are supercritical. This is because the solubility for ethene in the inert medium is greater in the supercritical state, such that more ethene is dissolved in the supercritical inert medium than in a liquid solvent. The process regime in the supercritical state therefore enables the use of a much higher proportion of ethene in a homogeneous mixture of ethene and inert medium than is possible on the basis of the thermodynamic solubility restriction in a purely liquid hydrocarbon stream. In this way, the space-time yield is distinctly enhanced. Since a greater amount of ethene can be passed into the reactor, it is possible as a result to better exploit the apparatus volume compared to a liquid phase process. The inert medium used may, for example, be isobutane.

16 Claims, 11 Drawing Sheets

Figure 1:
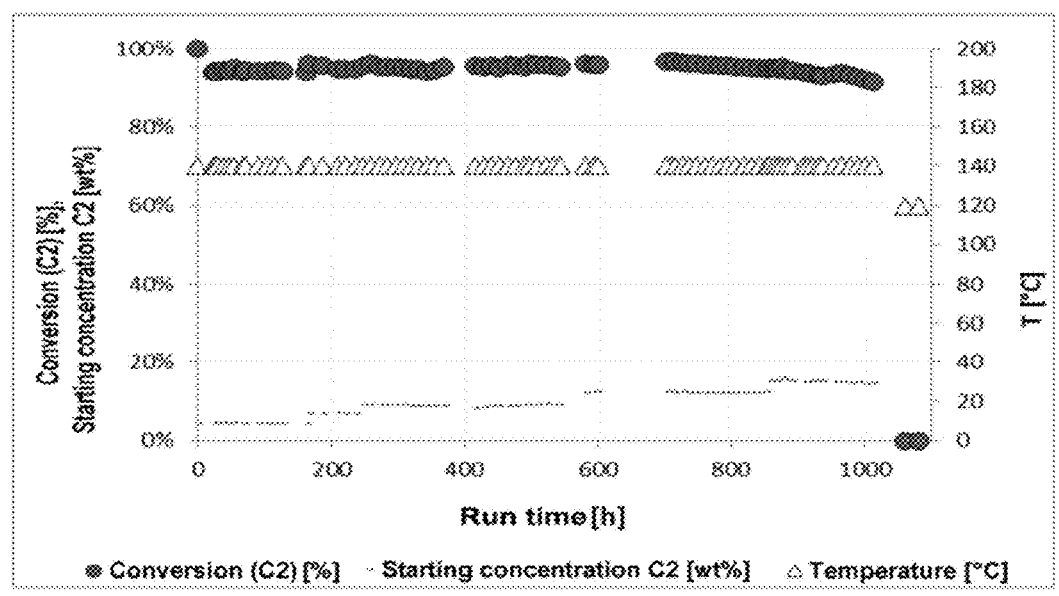

(51) Int. Cl.
*B01J 21/06* (2006.01)
*B01J 21/12* (2006.01)
*B01J 21/20* (2006.01)
*B01J 23/755* (2006.01)
*B01J 23/94* (2006.01)
*B01J 38/56* (2006.01)
*B01J 38/00* (2006.01)

(52) U.S. Cl.
CPC ............ *B01J 23/755* (2013.01); *B01J 23/94* (2013.01); *B01J 38/56* (2013.01); *B01J 2038/005* (2013.01); *C07C 2521/06* (2013.01); *C07C 2521/12* (2013.01); *C07C 2523/755* (2013.01)

(58) Field of Classification Search
USPC ......................................................... 585/504
See application file for complete search history.

(56) References Cited

U.S. PATENT DOCUMENTS

| | | |
|---|---|---|
| 7,294,741 B2 | 11/2007 | Bub et al. |
| 7,939,597 B2 | 5/2011 | Bub et al. |
| 8,198,481 B2 | 6/2012 | Kuppinger et al. |
| 8,258,249 B2 | 9/2012 | Bub et al. |
| 8,293,941 B2 | 10/2012 | Kuppinger et al. |
| 8,481,784 B2 | 7/2013 | Kuppinger et al. |
| 8,524,945 B2 | 9/2013 | Kuppinger et al. |
| 8,895,683 B2 | 11/2014 | Kuppinger et al. |
| 2004/0143043 A1* | 7/2004 | Gencer .................. C08J 3/205 524/105 |
| 2006/0194995 A1* | 8/2006 | Umansky ................. C10L 1/06 585/467 |
| 2009/0068440 A1 | 3/2009 | Bub et al. |
| 2009/0221862 A1* | 9/2009 | Beadle ...................... C07C 2/18 585/503 |
| 2012/0004489 A1* | 1/2012 | Mills ..................... B01J 19/1837 585/502 |
| 2013/0066128 A1 | 3/2013 | Breuil et al. |
| 2016/0207848 A1 | 7/2016 | Stochniol et al. |
| 2016/0207849 A1 | 7/2016 | Stochniol et al. |
| 2016/0257630 A1 | 9/2016 | Stochniol et al. |
| 2016/0276334 A1 | 12/2016 | Balduf et al. |
| 2017/0355651 A1* | 12/2017 | Reeker ..................... B01J 21/12 |

FOREIGN PATENT DOCUMENTS

| | | |
|---|---|---|
| EP | 3045439 A1 | 7/2016 |
| EP | 3064274 A1 | 9/2016 |
| WO | 9514647 A1 | 6/1995 |
| WO | 2005123633 A1 | 12/2005 |
| WO | 2010117539 A1 | 10/2010 |

OTHER PUBLICATIONS

Stochniol et al., U.S. Appl. No. 15/623,631, filed Jun. 15, 2017.
Friedlander et al., "Make Plasticizer Olefins Via N-Butene Dimerization," copyright Feb. 1986, Hydrocarbon Processing, pp. 31-33 (3 pages).
Nierlich, "Oligomerize for Better Gasoline," copyright Feb. 1992, Hydrocarbon Processing, pp. 45-46 (2 pages).
Zimmerman et al., "Ethylene," copyright 2012, Wiley-VCH Verlag GmbH & Co. KGaA, Weinheim, Ullmann's Encyclopedia of Industrial Chemistry, vol. 13, pp. 465-529 (65 pages).
European Search Report dated Dec. 5, 2016 in EP 16 173 939.6 (5 pages).

* cited by examiner

OLIGOMERIZATION OF ETHENE IN SUPERCRITICAL MODE

BACKGROUND

The invention is concerned with the oligomerization of supercritical ethene.

This application claims the benefit of European Application No. 16173939.6 filed on Jun. 10, 2016, the disclosure of which is expressly incorporated herein by reference.

Hydrocarbons are chemical compounds which consist exclusively of carbon and hydrogen. Alkenes (synonym: olefins) are hydrocarbons which have one C=C double bond in the molecule. Alkanes (synonym: paraffins), on the other hand, are hydrocarbons which have only single bonds. They are therefore also referred to as saturated.

In organic chemistry, hydrocarbons are frequently designated according to the number of carbon atoms which they have per molecule, in that the respective class of substances is preceded by the prefix $C_n$. "n" is the respective number of carbon atoms in a molecule. Thus, $C_4$ olefins are substances from the class of alkenes having four carbon atoms. $C_8$ olefins correspondingly have eight carbon atoms per molecule. Where the prefix $C_{n+}$ is used hereinafter, it refers to a class of substances which have more than n carbon atoms per molecule. A $C_{4+}$ olefin accordingly has at least five carbon atoms.

The simplest olefin is ethene (ethylene). It has two carbon atoms. Ethene is an important commodity chemical and is therefore prepared in large quantities. This is usually effected by cracking of naphtha. In addition, it can be obtained by dehydrogenation of ethane, which in turn is a constituent of natural gas. Owing to the increasing exploitation of unconventional sources of natural gas and decreasing recovery of petroleum, the proportion of ethene based on natural gas is steadily increasing. The physical properties of ethene and the preparation thereof are described in:

Zimmermann, Heinz and Walzl, Roland: Ethylene. Ullmann's Encyclopedia of Industrial Chemistry (2009).

Oligomerization is understood to mean the reaction of hydrocarbons with themselves, forming correspondingly longer-chain hydrocarbons, called the oligomers. Olefins having from two to eight carbon atoms can be oligomerized very readily.

Thus, for example, an olefin having six carbon atoms (hexene) can be formed by oligomerization of two olefins having three carbon atoms. The oligomerization of two molecules with one another is also referred to as dimerization. If, in contrast, three olefins having three carbon atoms are joined to one another (trimerization), the result is an olefin having nine carbon atoms. If n-butenes—i.e. olefins having four carbon atoms—are subjected to an oligomerization, the result is essentially olefins having eight carbon atoms (more specifically: dibutene), and additionally olefins having twelve carbon atoms ($C_{12}$ olefins, "tributene") and, to a smaller extent, olefins having more than twelve carbon atoms ($C_{12}+$ olefins).

Depending on the number of carbon atoms and what is called the degree of branching, the oligomers are used for the production of plasticizer esters or detergents or as a fuel additive:

Friedlander, Ward, Obenaus, Nierlich, Neumeister: Make plasticizer olefins via n-butene dimerization. Hydrocarbon Processing, February 1986, pages 31 to 33.

F. Nierlich: Oligomerize for better gasoline. Hydrocarbon Processing, February 1992, pages 45 to 46.

The oligomerization of ethene only becomes industrially practicable through use of catalysts. Industrial processes for oligomerization of ethene can be roughly divided into homogeneously catalysed processes and heterogeneously catalysed processes.

In homogeneously catalysed processes, the catalyst is dissolved in the reaction mixture. The reaction is effected in the liquid phase, in which the dissolved catalyst is also present. An advantage of homogeneous catalysis is the high efficiency of the reaction; a disadvantage is that the dissolved catalyst has to be separated from the reaction mixture in a costly and inconvenient manner. If the catalyst is very inexpensive (for example triethylaluminium) and catalyst residues do not impermissibly soil the oligomerizate, it is possible to dispense with a removal. Examples of homogeneously catalysed oligomerization of ethene are disclosed by WO2005/123633 and US2013/0066128.

In heterogeneously catalysed processes, the catalyst is in the solid state in the reactor. The ethene that flows through the reactor comes into contact with the solid catalyst. The oligomerizate is drawn off from the reactor and the solid catalyst remains in the reactor. An advantage of the heterogeneously catalysed processes is that the costly and inconvenient removal of catalyst is dispensed with and the reaction product is not contaminated by breakdown products of the catalyst. A disadvantage is that the catalyst is deactivated with time, especially in that polyethylene precipitates on the catalyst and blocks the catalytically active sites. The service life of the catalyst is therefore limited. A deactivated catalyst has to be either exchanged or regenerated.

Heterogeneous oligomerization can be effected either in the liquid phase or in the gaseous phase. Liquid phase oligomerization has the advantage that the reaction mixture has a greater density and hence the apparatus volume is more efficiently exploited. An advantage of the gas phase oligomerization of ethene is the lower pressures which make the apparatus less expensive and easier to control.

In addition, there are first approaches to oligomerizing ethene in the supercritical state:

WO1995/14647A1 claims a process for oligomerizing unbranched $C_2$ to $C_6$ olefins to dimers, trimers and tetramers by means of a fixed bed catalyst, in which the oligomerization is conducted in a reaction zone at supercritical temperature and supercritical pressure of the olefins used and no additional solvents that are not in the supercritical state in the reaction zone are used. The catalyst used comprises titanium dioxide, aluminium oxide, nickel oxide and silicon dioxide, and also alkali metal oxide resulting from the preparation. This catalyst is said to be of excellent suitability for oligomerization of butenes in butene/butane mixtures. However, the suitability thereof for the oligomerization of ethene is not discussed in WO1995/14647A1. There is a lack of specific details relating to the solvents used (substance, concentration, thermodynamic state). The emphasis of the contents of this publication is more on the production of the fixed bed catalyst than on the reaction regime.

WO2010/117539A2 discloses a process for oligomerizing ethene which occurs in a highly contaminated feed mixture. The feed mixture originates from a fluid-catalytic naphtha cracker (FCC) and comprises, as main constituents, methane and/or ethane, greater amounts of hydrogen and nitrogen, and carbon monoxide, carbon dioxide and hydrogen sulphide as impurities. It is mentioned in passing that the pressure can be conducted above the critical pressure of pure ethene; no specific details at all are given with regard to the critical temperature of ethene. The reaction is said to proceed essentially in the gas phase. It is a declared aim of WO2010/117539A2 to convert contaminated ethene-containing offgases to liquid fuels which can be added to the diesel or gasoline pool. Since the calorific value of the fuels rises with the number of carbon atoms in the hydrocarbons present therein, it makes sense to optimize such a process in the direction of production of longer-chain oligomers. In fact, the oligomerizate described in WO2010/117539A2 contains a large amount of olefins having ten or more carbon atoms.

By contrast, the processes optimized to the production of olefins having four to eight carbon atoms from ethene are those that are set out in some applications that were yet to be published at the priority date of this application. In said applications, ethene is oligomerized in the presence of at least one inert solvent. For instance, n-hexane is used as solvent in U.S. Ser. No. 15/000,807 or in EP 16151490.6, whereas propane or isobutane is preferred as solvent in U.S. Ser. No. 15/000,837 or in EP 15151624.2. In all cases, both the ethene and the solvent are in the liquid state.

Likewise still unpublished at present is European application 16158044.4 or U.S. Ser. No. 15/056,147, which describes the in situ regeneration of a solid catalyst used in ethene oligomerization. The regeneration is effected with the aid of a liquid purge medium which serves as solvent for the ethene in oligomerization operation. Purge media or solvents proposed are propane, isobutane, pentane, cyclopentane, hexane, cyclohexane, heptane or cycloheptane. Both in oligomerization operation and in regeneration operation, the solvent or purge medium is in the liquid state.

With regard to this prior art, the problem underlying the invention is that of specifying a process for oligomerization of ethene which enables a distinct rise in the space-time yield. In addition, a high selectivity in the direction of the dimers, trimers and tetramers of ethene is to be achieved.

Olefins having 10 or more carbon atoms ($C_{10+}$ olefins), by contrast, are barely to be formed. Furthermore, the process is to be efficient; more particularly, the apparatus volume is to be exploited to the best possible degree. A further important aim is the prolonging of the service life of the catalyst.

SUMMARY

These problems are solved by a heterogeneously catalysed process in which the oligomerization of ethene is conducted in the presence of an inert medium, wherein both the inert medium and the ethene are in the supercritical state. The inert medium is an alkane or a cycloalkane having not less than three and not more than seven carbon atoms. It is crucial that pressure and temperature of the mixture formed from ethene and inert medium are chosen with respect to the proportion of ethene in the mixture such that ethene and inert medium are in the supercritical state. Finally, the proportion by weight of the inert medium in the mixture should be selected so as to be greater than the proportion by weight of the ethene in the mixture.

A corresponding process is the subject-matter of the invention and is set out in Claim 1.

DETAILED DESCRIPTION

An essential aspect of the invention is that of mixing ethene with the inert medium and setting the conditions in the reaction such that both ethene and inert medium are supercritical. This is because the solubility for ethene in the inert medium is greater in the supercritical state, such that more ethene is dissolved in the supercritical inert medium than in a liquid solvent. The process regime in the supercritical state therefore enables the use of a much higher proportion of ethene in a homogeneous mixture of ethene and inert medium than is possible on the basis of the thermodynamic solubility restriction in a purely liquid hydrocarbon stream. In this way, the space-time yield is distinctly enhanced. Since a greater amount of ethene can be passed into the reactor, it is possible as a result to better exploit the apparatus volume compared to a liquid phase process.

In this context, it should be pointed out that, strictly speaking, there is no such thing as a solution in the supercritical state; instead, there are two coexisting supercritical phases within the mixture, namely that of ethene and that of inert medium. However, since the proportion by weight of the inert medium in the mixture is greater than that of the ethene, the inert medium acts analogously to a solvent in a liquid phase process. In this respect, the comparison that has just been set up between the "solubility" of supercritical ethene in supercritical inert medium and the solubility of liquid ethene in a liquid solvent is also permissible.

Solubility in the supercritical inert medium is increased not only for ethene, but also for unwanted by-products of the reaction, for instance polyethylene. Polyethylene is undesirable because it forms a waxy precipitate on the catalyst and the apparatuses, which lowers the activity of the catalyst and blocks the apparatuses. Since polyethylene has excellent solubility in supercritical alkanes or cycloalkanes having three to seven carbon atoms, the polyethylene is effectively washed away by the inert medium and the catalyst and the apparatuses are kept clean. The resulting extension of the service life of the catalyst is demonstrated by the experiments.

The physical reason for the fact that an alkane or a cycloalkane having three to seven carbon atoms is used as an inert medium in the process described here is that these substances can be put into the supercritical state at reasonable cost and inconvenience in a mixture with ethene; the temperatures and pressures required do not become too great: the critical pressures for the pure components mentioned vary between $27.4*10^5$ Pa for n-heptane and $50.4*10^5$ Pa for ethene. The critical temperatures are between 9.2° C. for ethene and 331° C. for cycloheptane. Thus, inert media having low molar mass are a particular option, since these have a lower critical temperature and the critical process parameters are accordingly achievable with low energy expenditure. It is therefore simpler to keep the mixture of ethene and inert medium in the supercritical state over the entire reaction period. This is because it is necessary to prevent one of the two components from leaving the critical state while still in the reactor and forming a liquid or gaseous phase.

It is likewise simple to provide a mixture of ethene with a $C_3$- to $C_7$-alkane or cycloalkane in the supercritical state before it is contacted with the heterogeneous catalyst. There are two options here:
a) inert medium is converted to the supercritical state by increasing the pressure and/or temperature and ethene is metered into the supercritical inert medium to obtain the supercritical mixture;
b) inert medium and ethene are mixed to give the mixture, and the mixture is converted to the supercritical state by increasing the temperature and/or pressure.

Both alternatives are easy to implement in terms of process technology.

From a chemical point of view, the alkanes and cycloalkanes are ideal inert media since—compared to ethene—they have virtually zero reactivity and hence do not take part in the oligomerization. They are inert in the reaction. Furthermore, they do not deactivate the catalyst to any significant degree.

If further substances apart from ethene and inert medium are present in the oligomerization, for instance production residues from the preparation processes therefor, these accompanying substances can quite possibly form a liquid or gaseous phase in the reaction mixture, since they do not of course take part in the reaction. The products of the reaction, i.e. the oligomers of ethene, may likewise form a liquid or gaseous phase. They are nevertheless discharged from the reactor by the supercritical inert medium. If such accompanying substances are likewise supercritical under the reaction conditions chosen, this is nevertheless harmless.

Ultimately, it is merely necessary for the mixture consisting of ethene and inert medium to be supercritical. Since the limit of the supercritical state of the mixture is defined by the pressure, temperature and ratio of ethene to inert medium, the pressure and temperature have to be adjusted with regard to the proportion of ethene in the mixture such that ethene and inert medium remain in the supercritical state.

If the reaction mixture comprises two or more alkanes and/or cycloalkanes having three to seven carbon atoms, it is sufficient when at least one of these substances is supercritical under the conditions chosen and therefore serves as inert medium.

The thermodynamic properties of the mixtures of ethene with the inert media specified here can be determined on the basis of available physical data for the pure substances with the aid of commercial simulation software. For the determination of the reaction conditions, the Aspen Properties V7.3 simulation software from Aspen Technology, Inc. was used here; the thermodynamic properties of the pure substances come from the APV73 database with PURE25, based on the release from the DIPPR database (January 2010).

The following substances are among the narrower selection of inert media: propane, isobutane, n-butane, n-pentane, isopentane, n-hexane, n-heptane, cyclopentane, cyclohexane, 2-methylpentane, 3-methylpentane, 2-methylhexane, 3-methylhexane, methylcyclopentane, methylcyclohexane. It is sufficient to use one of these substances as inert medium; it is also possible to mix two or more of these substances. Preference is given, however, to using only exactly one of these substances as inert medium, since it is then more easily possible to determine the thermodynamic properties of the binary mixture of ethene and inert medium.

If the inert medium used is solely isobutane, the proportion of ethene in the mixture on commencement of contact with the catalyst should be between 4% by weight and 30% by weight, the pressure of the mixture should be between $25*10^5$ Pa and $100*10^5$ Pa, and the temperature of the mixture should be adjusted to a value between 90° C. and 200° C. These three parameters may admittedly not be selected independently from the range specified, but always with the proviso that both ethene and isobutane are in the supercritical state. Value triples that fulfil this condition are found by the simulation software.

The fewer accompanying substances aside from ethene and the inert medium that are present in the oligomerization, the simpler it is to assure the supercritical state of the ethene and of the inert medium. The ethene used in the process should be very substantially free of impurities or accompanying substances. Preference is given to using commercially available ethene of "polymer grade" purity; this typically has a purity of more than 99.9%.

If the mixture of ethene and inert medium is used together with at least one accompanying substance as reactant mixture for the process, the reactant mixture on commencement of contact with the catalyst should have the following composition that adds up to 100% by weight:
Isobutane: 70% by weight to 96% by weight;
Ethene: 4% by weight to 30% by weight;
Sum of all accompanying substances: more than 0% by weight to a maximum of 5% by weight.

The sum of all accompanying substances encompasses all substances that are present on commencement of contact of the reactant mixture with the catalyst apart from the isobutane and the ethene.

It will be apparent to specialists in the field that the reactant mixture specified here is very clean compared to the feed used in WO2010/117539A2. This has a positive effect on the product composition and the process intensity.

As a result of the oligomerization that commences with the contact, the composition of the product mixture drawn off from the catalyst is much more complex than that of the reactant mixture.
Isobutane: 70% by weight to 96% by weight;
Ethene: 0% by weight to 2% by weight;
Olefins having four carbon atoms: 2.3% by weight to 21% by weight;
Olefins having six carbon atoms: 0.9% by weight to 7.2% by weight;
Olefins having eight carbon atoms: 0.1% by weight to 6.3% by weight;
Olefins having ten carbon atoms: 0% by weight to 3% by weight;
Olefins having twelve carbon atoms: 0% by weight to 2.7% by weight;
Sum of all other constituents: 0% by weight to 5% by weight.

It will be apparent that all constituents of the product mixture according to this specification add up to 100% by weight.

At this point it will be apparent to expert readers that predominantly dimers, trimers and tetramers of ethene are formed, while the selectivity of the reaction in the direction of the higher oligomers having ten or more carbon atoms is low. The product mixture accordingly differs distinctly from the oligomerizate formed in WO2010/117539A2.

Just like isobutane, n-hexane is of excellent suitability as inert medium. Because of the thermodynamic properties of n-hexane, the proportion of ethene in the mixture on commencement of contact with the catalyst should be between 5% by weight and 30% by weight, the pressure of the mixture should be adjusted to a value between $25*10^5$ Pa and $100*10^5$ Pa, and the temperature of the mixture should be between 90° C. and 250° C., again with the proviso that both ethene and n-hexane are in the supercritical state.

The process presented here for oligomerization of ethene in supercritical mode is heterogeneously catalysed. The catalyst used is therefore in the solid state. A suitable catalyst comprises at least two components, where the first component comprises at least one element selected from Ni, Cr, Fe, Ti which is in metallic and/or oxidic and/or hydridic form and the second component comprises at least one metal oxide selected from $Al_2O_3$, $SiO_2$, $TiO_2$, $ZrO_2$. An example of a catalyst of this kind is known from U.S. Pat. No. 2,581,228. WO1995/14647A1 also describes the preparation of a suitable fixed bed catalyst, although the suitability of this catalyst for ethene oligomerization is not apparent from this document.

In spite of the use of supercritical inert medium with good solubility for the substances that deactivate the catalyst, the service life of the catalyst is limited. In order to make a gradually deactivated catalyst fully usable again, regeneration is possible. The regeneration is effected by purging the catalyst with a purge medium, but one that should be liquid in order to remove the deposits on the catalyst. The regeneration can be effected in situ, i.e. in the reactor. The catalyst in that case need not be deinstalled for the regeneration, which distinctly lowers the operating costs. There is accordingly cyclical alternation between an oligomerization operation and a regeneration operation.

The invention therefore also provides a combination of the process described here for oligomerization of ethene in supercritical mode with a process for regeneration of the catalyst used in the oligomerization, having the following features:

a) the oligomerization is effected in an oligomerization operation in which the inert medium and ethene, each in the supercritical state, are contacted with the catalyst;

b) the regeneration is effected in a regeneration operation in which the catalyst in the absence of ethene, hydrogen and oxygen is purged with a liquid purge medium;

c) operation is interchanged over time between the oligomerization operation and the regeneration operation, in such a way that a time-limited oligomerization operation is followed by a time-limited regeneration operation, and the latter in turn is followed by a time-limited oligomerization operation;

d) the catalyst is always at the same location, which is the reason why both oligomerization operation and regeneration operation take place at this location;

e) the location of the catalyst is supplied with positive or negative thermal energy in order to impose a set temperature thereon, it being entirely possible for the actual temperature at the catalyst to deviate from the set temperature in a time- and space-limited manner;

f) the set temperature in regeneration operation is lower than the set temperature in oligomerization operation;

g) the pressure at the location of the catalyst is lower in regeneration operation than in oligomerization operation.

In a particularly preferred development of this combination, the purge medium and inert medium used is the same substance, with the proviso that this substance is in the supercritical state in oligomerization operation and in the liquid state in regeneration operation. This is because it has been found that, surprisingly, the substances described here as suitable inert media are also suitable as purge media. In order to interchange between oligomerization operation and regeneration operation, it is therefore necessary merely to shut down the ethene feed and lower the pressure and temperature, in order to convert the supercritical inert medium to a liquid purge medium. The interchange operation is therefore very rapid and amenable to automation.

If the purge medium and inert medium used is isobutane, the pressure in oligomerization operation is adjusted to a value between $45*10^5$ Pa and $55*10^5$ Pa and the temperature in oligomerization operation is adjusted to a value between 125° C. and 155° C., the pressure and temperature are simply lowered in regeneration operation, namely to a pressure between $25*10^5$ Pa and $35*10^5$ Pa and to a temperature between 105° C. and 125° C.

In this way, the catalyst can be rapidly regenerated with low cost and inconvenience. Since shutdown periods constitute an immense cost driver in sustained industrial production, the combination of oligomerization and regeneration described here is very economically viable.

The process is now to be elucidated in detail with reference to examples. The corresponding graphs show:

FIG. 1: Ethylene oligomerization under supercritical conditions (for Example 1)

Figure 2:
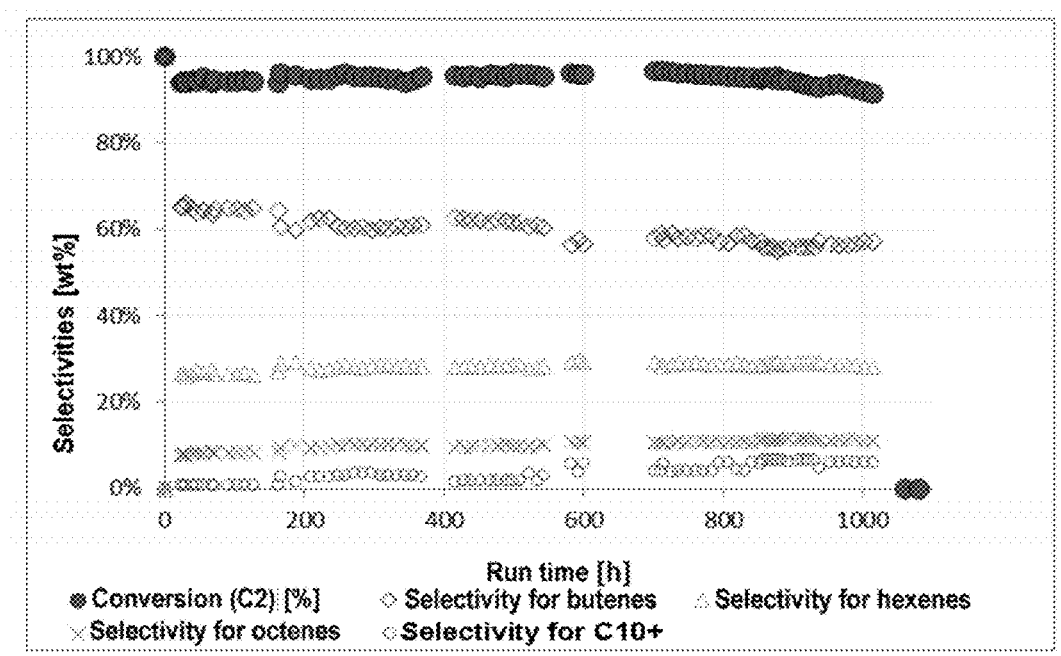

FIG. 2: Product distribution from ethylene oligomerization under supercritical conditions (for Example 1)

Figure 3:
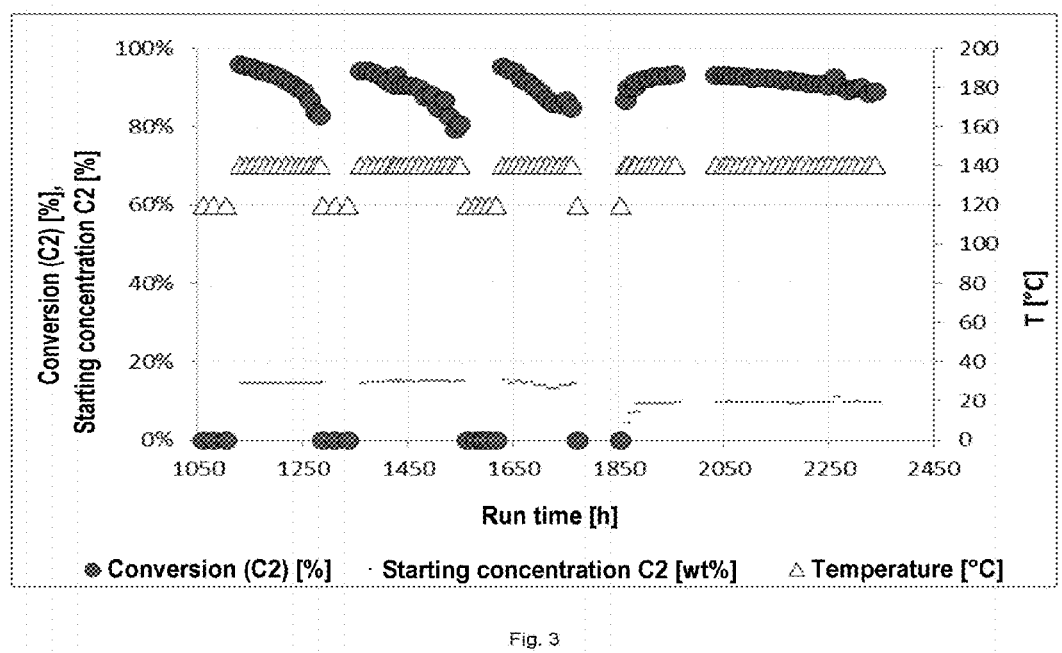

FIG. 3: Ethylene oligomerization under supercritical conditions and in situ regeneration by means of liquid isobutane in alternation (for Example 2)

Figure 4:
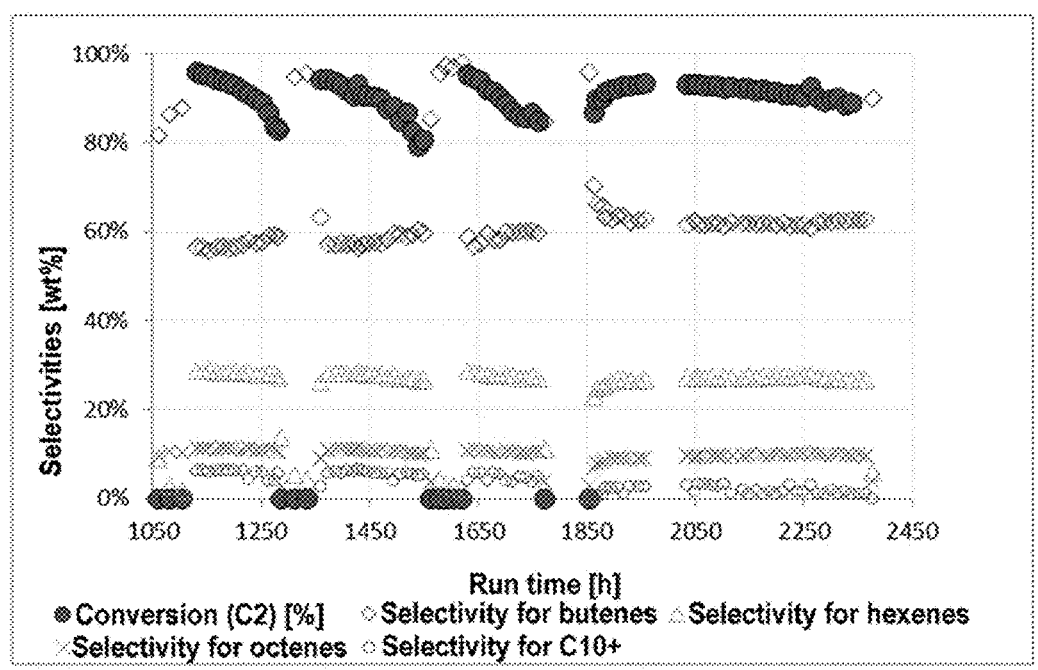

FIG. 4: Product distribution from ethylene oligomerization under supercritical conditions and in situ regeneration by means of liquid isobutane in alternation (for Example 2)

Figure 5:
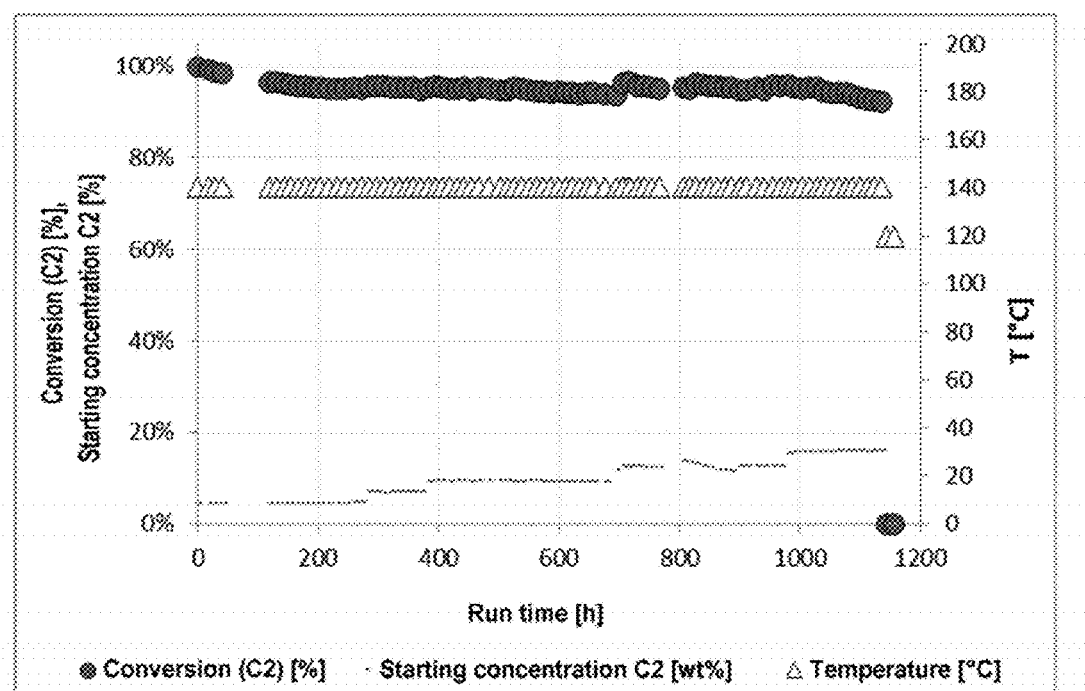

FIG. 5: Example of ethylene oligomerization under supercritical conditions (for Example 3)

Figure 6:
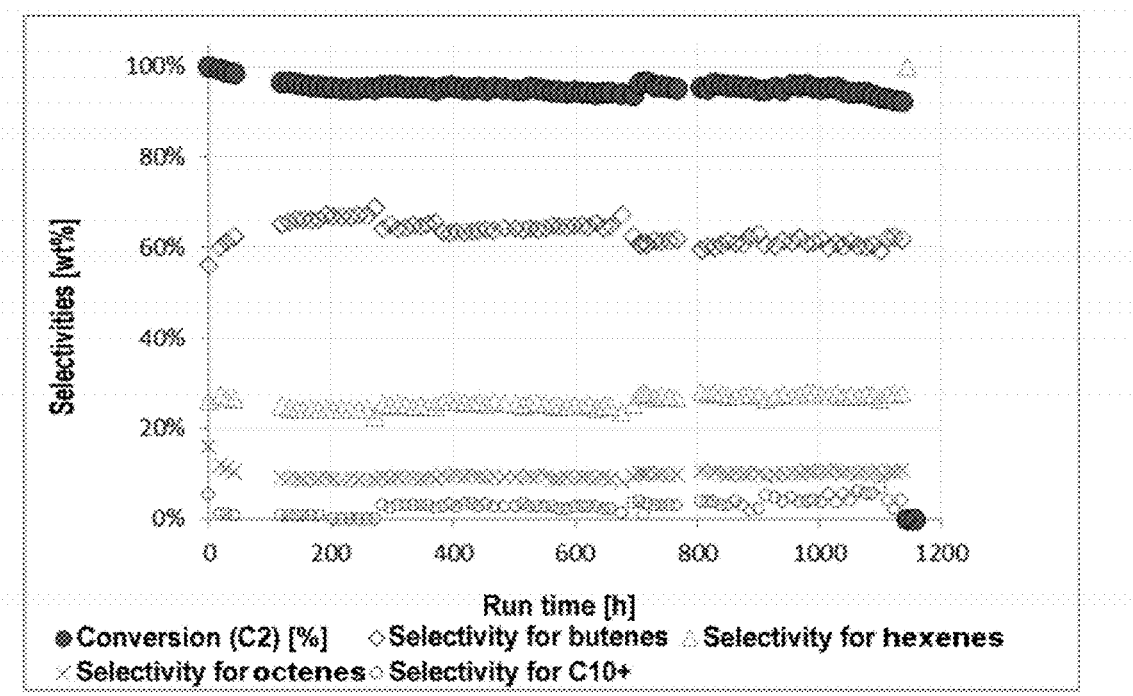

FIG. 6: Product distribution from ethylene oligomerization under supercritical conditions (for Example 3)

Figure 7:
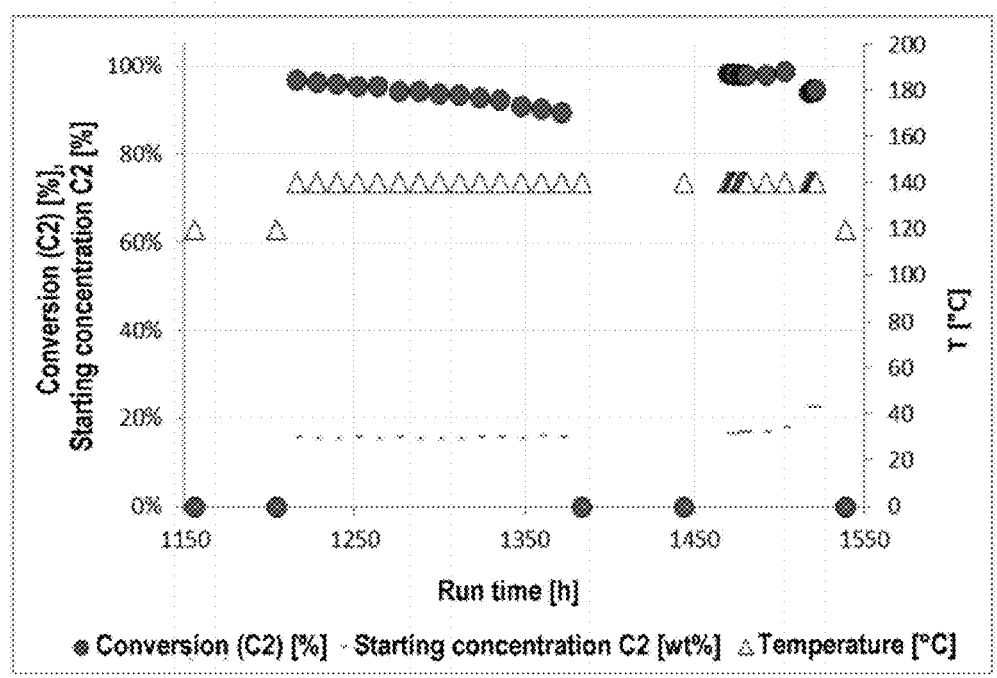

FIG. 7: Ethylene oligomerization under supercritical conditions and in situ regeneration by means of liquid isobutane in alternation (for Example 4)

Figure 8:
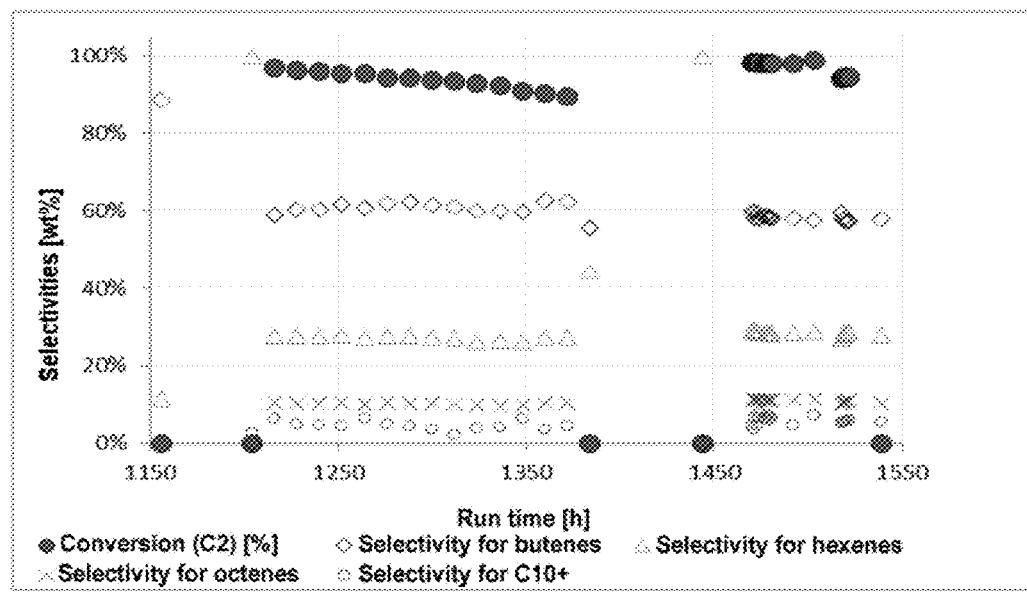

FIG. 8: Product distribution from ethylene oligomerization under supercritical conditions and in situ regeneration by means of liquid isobutane in alternation (for Example 4)

Figure 9:
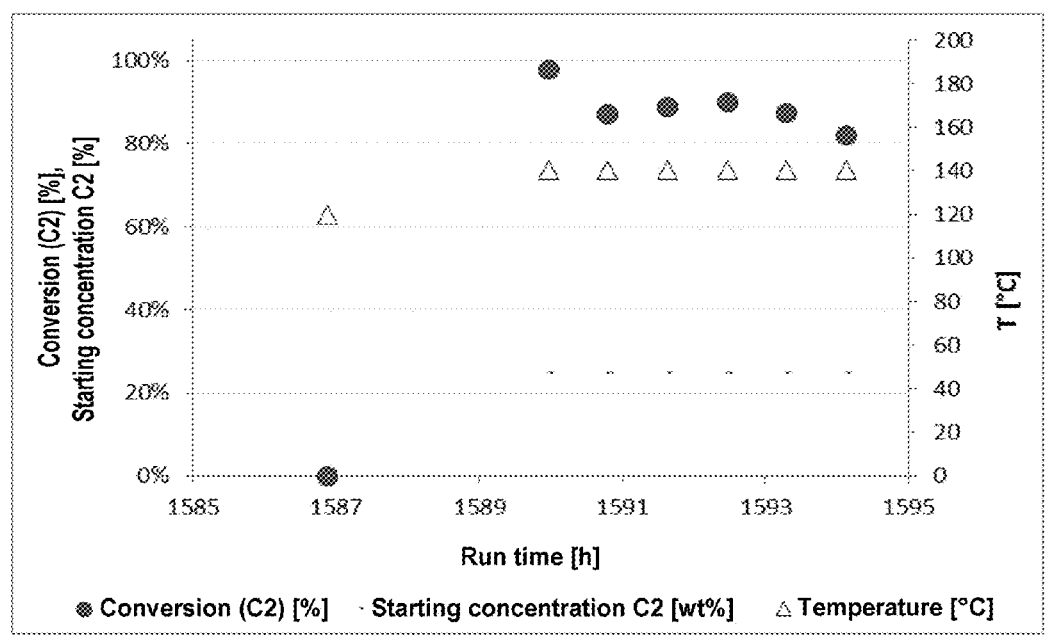

FIG. 9: Ethylene oligomerization below the critical pressure of the feed mixture (for Counterexample 5)

Figure 10:
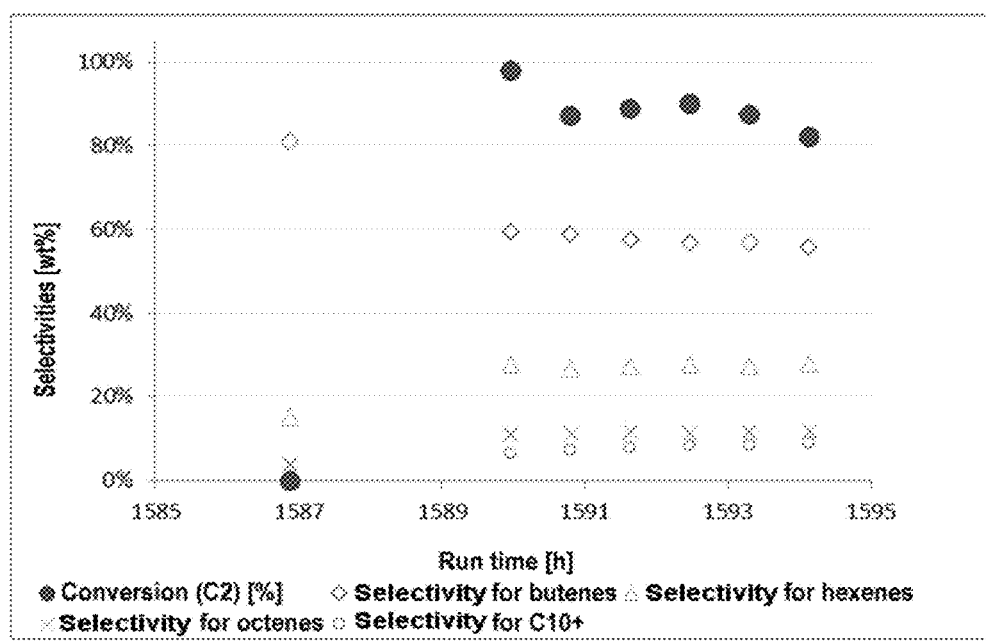

FIG. 10: Product distribution from ethylene oligomerization below the critical pressure of the feed mixture (for Counterexample 5)

Figure 11:
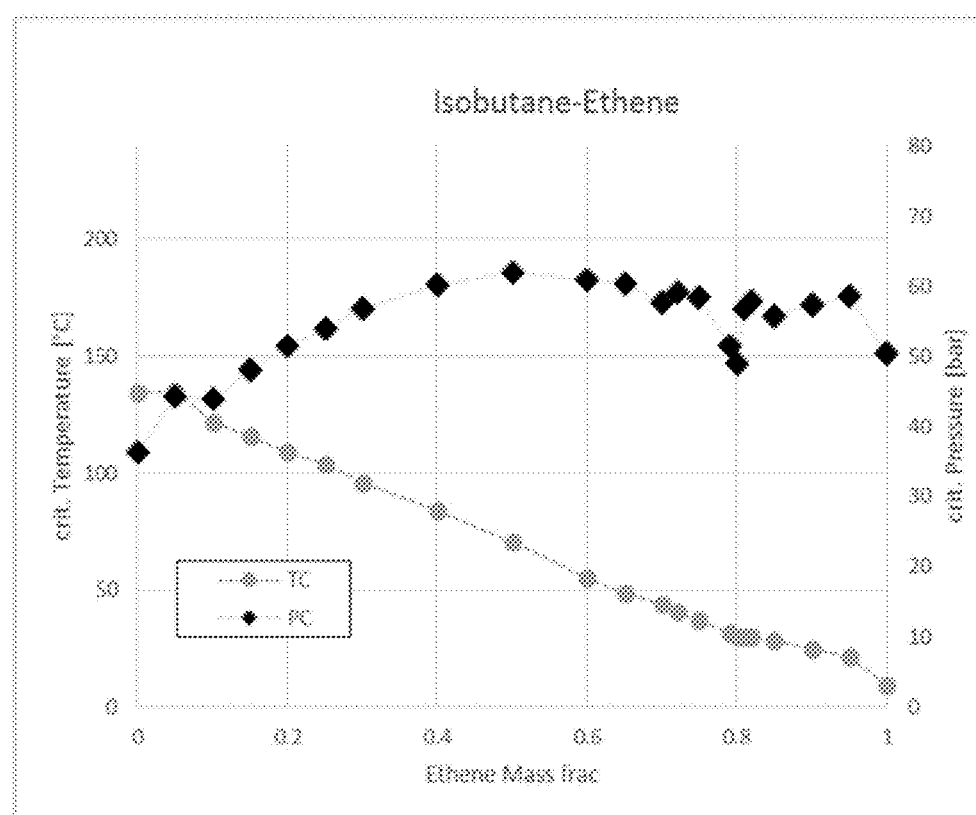

FIG. 11: Calculated critical data of a binary mixture of isobutane and ethene.

EXAMPLE 1: ETHYLENE OLIGOMERIZATION IN ISOBUTANE UNDER SUPERCRITICAL CONDITIONS 12.6 g of a heterogeneous catalyst based on nickel, titanium dioxide and silica-alumina (prepared according to WO9514647A1) were introduced into an externally oil-heated and -cooled tubular reactor of length 1 m and internal diameter 6 mm. Subsequently, a mixture of 4% by mass to 15% by mass of ethene and 85% by mass to 96% by mass of isobutane, after the pressure had been increased to 50 bar, was run continuously over the catalyst at a total flow rate of 120 g/h at a temperature of 140° C. (weight hourly space velocity WHSV=9.5 $h^{-1}$ based on the overall feed). The pressure was kept constant at 50 bar (50 bar corresponds to $50*10^5$ Pa). After a time of approximately 23 hours, a state in which there was no further change in conversion had been attained.

FIG. 1 shows the conversion plot including the proportion of ethylene fed in as a function of the run time of the reaction. The ethene conversion is marked by the solid dot •, the starting concentration of ethene by a dash -, and the temperature by a triangle Δ.

Over the course of 600 h, a relatively constant ethylene conversion of about 95% was recorded. Only in the case of an ethylene content of more than 12% in the feed was there minimal deactivation, and this progressed ever further, such that, after a further run time of nearly 300 h, the conversion dropped to 91% and the regeneration of the catalyst was commenced.

In FIG. 2, the selectivities achieved were plotted. The diamond ◇ marks the selectivity for the butenes, the triangle Δ the selectivity for the hexenes, the cross X the selectivity for the octenes, and the circle ○ the selectivity for the $C_{10+}$ olefins.

As apparent from FIG. 2, over the entire run time of the experiment, a slightly falling butene selectivity was observed, commencing at 65%. It reached a value of about 57% after a run time of about 1000 h. The further product fractions, by contrast, showed a slight rise in their selectivity of about 2 to 4 percentage points in each case.

EXAMPLE 2: ETHYLENE OLIGOMERIZATION UNDER SUPERCRITICAL CONDITIONS AND IN SITU REGENERATION BY MEANS OF THE LIQUID INERT MEDIUM ISOBUTANE IN ALTERNATION

For regeneration, the experiment with the catalyst from Example 1 was continued. The ethene feed was stopped and the total flow rate was increased to 167 g/h to accelerate the purging operation. The temperature was lowered to 120° C. and the pressure to 30 bar (30*$10^5$ Pa). After a respective regeneration interval of 75 h to 98 h, the fine filter that was kept at room temperature and 30 bar beyond the plant was checked and changed if required. Then ethylene was mixed in again, and the total flow rate was lowered to 120 g/h, while the temperature was increased to 140° C. and the pressure to 50 bar. This operation was repeated several times as soon as the ethylene conversion had dropped noticeably after a run time of 130 h to 188 h in each case, or the installed filter suggested polymer deposits by the indication of an increase in the pressure differential. Overall, 94 mg of polyethylene were recovered from the filter, mainly as fine powder, over the course of the experiment, which accounts for much less than 0.01% of the total amount of ethylene used.

FIG. 3 shows the regeneration intervals described in the liquid phase (intervals at 120° C.) in alternation with intervals of ethene oligomerization under supercritical conditions (intervals at 140° C.). The ethene conversion is again marked by the solid dot •, the starting concentration of ethene by a dash -, and the temperature by a triangle Δ.

The selectivities achieved were plotted in the graph of FIG. 4. The diamond 0 marks the selectivity for the butenes, the triangle Δ the selectivity for the hexenes, the cross X the selectivity for the octenes, and the circle ○ the selectivity for the $C_{10+}$ olefins. FIG. 4 shows that the regeneration in conjunction with the supercritical mode of operation enables restoration of the initial selectivities from Example 1. The butene selectivity increases again over the course of the run time from 56% to 63%, while the selectivities for the hexene and octene fractions each fall by 2 percentage points. The advantage of the supercritical mode of operation becomes particularly clear in the $C_{10+}$ fraction; the selectivity value falls considerably from 6% to 1%.

Comparison of Examples 1 and 2

Examples 1 and 2 show that it is possible to conduct ethene oligomerization under supercritical conditions with an ethylene content up to 15% over a long period at very high conversions of 80% to 99% continuously over a notable run time of more than 2000 h when the reaction is effected alternately with regeneration intervals in the liquid phase, the regeneration time and frequency depending on the ethylene content in the mixture and being about 14% of the total run time in the present example. As shown, the regeneration can be implemented without the necessity for dismantling of the reactor, but in a simple manner in situ by purging with liquid inert medium after the ethylene has been shut down and pressure and temperature have been lowered.

Moreover, it is apparent from Example 2 that the supercritical mode of operation in combination with regular regeneration is capable of restoring and maintaining the very good initial selectivities.

EXAMPLE 3: ETHYLENE OLIGOMERIZATION IN ISOBUTANE UNDER SUPERCRITICAL CONDITIONS 19.3 g of a heterogeneous catalyst based on nickel and silica-alumina (prepared according to U.S. Pat. No. 2,581, 228) were introduced into a tubular reactor which had a length of 1 m and an internal diameter of 6 mm and whose temperature was controlled from the outside by means of oil. Subsequently, a mixture of 4% by mass to 17% by mass of ethene and 83% by mass to 96% by mass of isobutane, after the pressure had been increased to 50 bar, was run continuously over the catalyst at a total flow rate of 125 g/h at a temperature of 140° C. at a weight hourly space velocity (WHSV) of 6.5 $h^{-1}$ based on the overall feed. The pressure was kept constant at 50 bar.

FIG. 5 shows the conversion plot as a function of the run time of the reaction and the proportion of ethylene fed in the reactor. The ethene conversion is marked by the solid dot •, the starting concentration of ethene by a dash -, and the temperature by a triangle Δ.

After slight initial deactivation of the catalyst, a relatively constant ethylene conversion of about 95% was recorded over 860 h. Only in the case of an ethylene content of more than 13% in the feed was there minimal deactivation, and this progressed ever further, such that, after a further run time of nearly 144 h, the conversion dropped to 92% and the regeneration of the catalyst was commenced.

In FIG. 6, the selectivities achieved in Experiment 3 were plotted. The diamond 0 marks the selectivity for the butenes, the triangle Δ the selectivity for the hexenes, the cross X the selectivity for the octenes, and the circle ○ the selectivity for the $C_{10+}$ olefins. It is apparent from FIG. 6 that the product selectivities are at a comparable level to Example 1. The evolution thereof over the run time is also virtually identical.

EXAMPLE 4: ETHYLENE OLIGOMERIZATION UNDER SUPERCRITICAL CONDITIONS AND IN SITU REGENERATION BY MEANS OF THE LIQUID INERT MEDIUM ISOBUTANE IN ALTERNATION

For regeneration, the experiment with the catalyst from Example 3 was continued. The ethylene feed was stopped and the total flow rate was increased to 167 g/h to accelerate the purging operation. The temperature was lowered to 120° C. and the pressure to 30 bar. After a respective regeneration interval of 50 h to 60 h, the fine filter that was kept at room temperature and 30 bar beyond the plant was checked and changed if required. Then ethylene was mixed in again, and the total flow rate was lowered to 120 g/h, while the temperature was increased to 140° C. and the pressure to 50 bar. The mixture varied between 15% by mass and 25% by mass of ethene and 75% by mass to 85% by mass of isobutane. The regeneration operation was repeated several times as soon as the ethylene conversion had dropped noticeably after a run time of 50 h to 160 h in each case, or the installed filter suggested polymer deposits by the indication of an increase in the pressure differential. Overall, 350 mg of polyethylene were recovered from the filter, mainly as fine powder, over the course of the experiment, which accounts for much less than 0.01% of the total amount of ethylene used.

FIG. 7 shows the regeneration intervals described in the liquid phase (intervals at 120° C.) in alternation with intervals of ethylene oligomerization under supercritical conditions (intervals at 140° C.). The ethene conversion is marked by the solid dot •, the starting concentration of ethene by a dash -, and the temperature by a triangle Δ.

FIG. 8 shows the corresponding product distribution between the regeneration cycles. The diamond 0 marks the selectivity for the butenes, the triangle Δ the selectivity for the hexenes, the cross X the selectivity for the octenes, and the circle ○ the selectivity for the $C_{10+}$ olefins. As apparent, it is possible by means of the combination of supercritical mode and regeneration to keep the product distribution at least constant even in the case of very high ethylene contents in the feed.

Discussion of Examples 3 and 4

Examples 3 and 4 show that it is likewise possible to conduct ethylene oligomerization under supercritical conditions with an ethylene content of more than 15% and of up to 23% over a long period at very high conversions of 80% to 99% and constant product selectivities continuously over a notable run time of more than 1550 h when the reaction is effected alternately with regeneration intervals in the liquid phase, the regeneration time and frequency of the regeneration depending on the ethylene content in the mixture and being about 4% of the total run time in the present example. As shown, the regeneration can be implemented without the necessity for dismantling of the reactor, but in a simple manner in situ by purging with liquid inert medium after the ethylene has been shut down and pressure and temperature have been lowered.

COUNTEREXAMPLE 5: ETHYLENE OLIGOMERIZATION OUTSIDE THE SUPERCRITICAL RANGE AS A RESULT OF TOO HIGH AN ETHYLENE CONCENTRATION

After a regeneration phase for 50 h under the same conditions as in the previous examples, the experiment was continued with the catalyst from Examples 3 and 4. Then ethylene was mixed in again, and the total flow rate was lowered to 120 g/h, while the temperature was increased to 140° C. and the pressure to 50 bar. The feed mixture contained 25% by mass of ethene and 75% by mass of isobutane. The conversion fell significantly to 82% within 5 h. This rapid deactivation is the result of the pressure being below the critical pressure, which is about 54 bar with this proportion of ethylene in the mixture with isobutane. Moreover, within this very short period of time, in parallel with the conversion, the selectivity for butenes also dropped from 60% to 56%, while there was a distinct increase in the $C_{10+}$ fraction from 6% to 9%. It was thus shown that compliance with supercritical conditions is essential for high activity, stability and selectivity of the process. FIGS. 9 and 10 show the ethene oligomerization interval described from a run time of 1590 h outside the critical phase. The marking symbols were chosen in accordance with the other graphs.

Discussion of Counterexample 5

Counterexample 5 shows that it is crucial to conduct ethylene oligomerization under supercritical conditions of the feed mixture. Specifically when the pressure of the mixture is below the critical pressure, the catalyst is deactivated rapidly with simultaneous significant loss of selectivity for the short-chain desired products having four to eight carbon atoms within a few hours.

With increasing ethene content in the feed mixture, there is a rise in the critical pressure of the mixture with a maximum around 50% by weight of ethene. This relationship is also apparent in FIG. 11. The critical pressures (diamond ◊) and critical temperatures (solid circle ●) were calculated with the Aspen Properties V7.3 software from Aspen Technology. The thermodynamic properties of ethene and isobutane that are required for the calculation come from the APV73 material database with PURE25, based on the release of the DIPPR database (January 2010).

The invention claimed is:

1. A process for oligomerizing ethene, comprising:
   (I) an oligomerization operation, in which a mixture comprising ethene and an inert medium contacts a solid catalyst, wherein the proportion by weight of the inert medium in the mixture is greater than the proportion by weight of ethene in the mixture, wherein the inert medium is a $C_3$-$C_7$ alkane or a $C_3$-$C_7$ cycloalkane, wherein the pressure and temperature of the mixture are chosen with respect to the proportion by weight of ethene in the mixture such that the ethene and the inert medium are in the supercritical state, and wherein the ethene and the inert medium each contact the solid catalyst in the supercritical state; and
   (II) a regeneration operation, in which the solid catalyst in the absence of ethene, hydrogen, and oxygen is purged with a liquid purge medium, wherein:
   a) operation is interchanged over time between the oligomerization operation and the regeneration operation, in such a way that a time-limited oligomerization operation is followed by a time-limited regeneration operation, and the latter in turn is followed by a time-limited oligomerization operation;
   b) the solid catalyst is always at the same location during both the oligomerization operation and the regeneration operation;
   c) the location of the solid catalyst is supplied with positive or negative thermal energy in order to impose a set temperature thereon during both the oligomerization operation and the regeneration operation;
   d) the set temperature in the regeneration operation is lower than the set temperature in the oligomerization operation; and
   e) the pressure at the location of the solid catalyst is lower in the regeneration operation than in the oligomerization operation.

2. The process according to claim 1, wherein the mixture is at first provided in the supercritical state and then contacted with the solid catalyst, where the provision of the mixture in the supercritical state is affected either according to alternative a) or according to alternative b):
   a) the inert medium is converted to the supercritical state by increasing the pressure and/or temperature of the inert medium and ethene is metered into the supercritical inert medium to obtain the supercritical mixture;
   b) the inert medium and ethene are mixed to give the mixture, and the mixture is converted to the supercritical state by increasing the temperature and/or pressure of the mixture.

3. The process according to claim 1, wherein the inert medium is selected from the group consisting of propane, isobutane, n-butane, isopentane, n-pentane, n-hexane, n-heptane, cyclopentane, cyclohexane, 2-methylpentane, 3-methylpentane, 2-methylhexane, 3-methylhexane, methylcyclopentane, or methylcyclohexane.

4. The process according to claim 3, wherein the inert medium is isobutane, and wherein the proportion of ethene in the mixture on commencement of contact with the solid catalyst is between 4% by weight and 30% by weight, the pressure of the mixture is adjusted to a value between $25*10^5$ Pa and $100*10^5$ Pa, and the temperature of the mixture is adjusted to a value between 90° C. and 200° C., wherein both ethene and isobutane are in the supercritical state.

5. The process according to claim 4, wherein the mixture is provided as a reactant mixture together with at least one accompanying substance, where the reactant mixture on commencement of contact with the solid catalyst has the following composition that adds up to 100% by weight:
Isobutane: 70% by weight to 96% by weight;
Ethene: between 4% by weight and 30% by weight;
Sum of all accompanying substances: more than 0% by weight to a maximum of 5% by weight.

6. The process according to claim 4, wherein a product mixture having the following composition that adds up to 100% by weight is drawn off from the solid catalyst:
Isobutane: 70% by weight to 96% by weight;
Ethene: 0% by weight to 2% by weight;
Olefins having four carbon atoms: 2.3% by weight to 21% by weight;
Olefins having six carbon atoms: 0.9% by weight to 7.2% by weight;
Olefins having eight carbon atoms: 0.1% by weight to 6.3% by weight;
Olefins having ten carbon atoms: 0% by weight to 3% by weight;
Olefins having twelve carbon atoms: 0% by weight to 2.7% by weight;
Sum of all other constituents: 0% by weight to 5% by weight.

7. The process according to claim 3, wherein the inert medium is n-hexane, wherein the proportion of ethene in the mixture on commencement of contact with the solid catalyst is between 5% by weight and 30% by weight, the pressure of the mixture is adjusted to a value between $25*10^5$ Pa and $100*10^5$ Pa, and the temperature of the mixture is adjusted to a value between 90° C. and 250° C., wherein both ethene and n-hexane are in the supercritical state.

8. The process according to claim 1, wherein the solid catalyst comprises at least two components, where the first component comprises at least one element selected from Ni, Cr, Fe, or Ti which is in metallic, oxidic, or hydridic form, and where the second component comprises at least one metal oxide selected from the group consisting of $Al_2O_3$, $SiO_2$, $TiO_2$, and $ZrO_2$.

9. The combination process according to claim 1, wherein the liquid purge medium and the inert medium is the same substance.

10. The process according to claim 9, wherein the liquid purge medium and the inert medium is isobutane, wherein the pressure in the oligomerization operation is adjusted to a value between $45*10^5$ Pa and $55*10^5$ Pa and the temperature in the oligomerization operation is adjusted to a value between 125° C. and 155° C., and wherein the pressure in the regeneration operation is adjusted to a value between $25*10^5$ Pa and $35*10^5$ Pa and the temperature in the regeneration operation is adjusted to a value between 105° C. and 125° C.

11. The process according to claim 2, wherein the inert medium is one of the following substances: propane, isobutane, n-butane, isopentane, n-pentane, n-hexane, n-heptane, cyclopentane, cyclohexane, 2-methylpentane, 3-methylpentane, 2-methylhexane, 3-methylhexane, methylcyclopentane, or methylcyclohexane.

12. The process according to claim 5, wherein a product mixture having the following composition that adds up to 100% by weight is drawn off from the solid catalyst:
Isobutane: 70% by weight to 96% by weight;
Ethene: 0% by weight to 2% by weight;
Olefins having four carbon atoms: 2.3% by weight to 21% by weight;
Olefins having six carbon atoms: 0.9% by weight to 7.2% by weight;
Olefins having eight carbon atoms: 0.1% by weight to 6.3% by weight;
Olefins having ten carbon atoms: 0% by weight to 3% by weight;
Olefins having twelve carbon atoms: 0% by weight to 2.7% by weight;
Sum of all other constituents: 0% by weight to 5% by weight.

13. The process according to claim 2, wherein the solid catalyst comprises at least two components, where the first component comprises at least one element selected from Ni, Cr, Fe, or Ti which is in metallic, oxidic, or hydridic form, and where the second component comprises at least one metal oxide selected from the group consisting of $Al_2O_3$, $SiO_2$, $TiO_2$, and $ZrO_2$.

14. The process according to claim 3, wherein the solid catalyst is in the solid state and comprises at least two components, where the first component comprises at least one element selected from the group consisting of Ni, Cr, Fe, and Ti which is in metallic, oxidic, or hydridic form, and where the second component comprises at least one metal oxide selected from the group consisting of $Al_2O_3$, $SiO_2$, $TiO_2$, and $ZrO_2$.

15. The process according to claim 4, wherein the solid catalyst comprises at least two components, where the first component comprises at least one element selected from the group consisting of Ni, Cr, Fe, and Ti which is in metallic, oxidic, or hydridic form, and wherein the second component comprises at least one metal oxide selected from the group consisting of $Al_2O_3$, $SiO_2$, $TiO_2$, and $ZrO_2$.

16. The process according to claim 2, wherein the liquid purge medium and the inert medium is the same substance.

* * * * *